United States Patent
Kano et al.

(10) Patent No.: US 8,298,229 B2
(45) Date of Patent: Oct. 30, 2012

(54) BODY TISSUE INCISION APPARATUS

(75) Inventors: Akihito Kano, Tokyo (JP); Hideyuki Kasahara, Tokyo (JP); Seiji Maeda, Tokyo (JP); Randal J. Kadyowski, South Lyon, MI (US); Lyne M. Charron-Keller, Brighton, MI (US)

(73) Assignees: Terumo Cardiovascular Systems Corporation, Ann Arbor, MI (US); Olympus Medical Systems Corporation, Tokyo (JP)

( * ) Notice: Subject to any disclaimer, the term of this patent is extended or adjusted under 35 U.S.C. 154(b) by 1091 days.

(21) Appl. No.: 12/136,388

(22) Filed: Jun. 10, 2008

(65) Prior Publication Data

US 2009/0306541 A1    Dec. 10, 2009

(51) Int. Cl.
*A61B 18/14* (2006.01)

(52) U.S. Cl. .......................................... 606/48; 606/51

(58) Field of Classification Search ............ 606/41, 606/45–52
See application file for complete search history.

(56) References Cited

U.S. PATENT DOCUMENTS

| | | |
|---|---|---|
| 2006/0206112 A1 | 9/2006 | Kasahara |
| 2007/0078459 A1* | 4/2007 | Johnson et al. ............ 606/51 |
| 2008/0208193 A1* | 8/2008 | Yamatani et al. .......... 606/48 |

FOREIGN PATENT DOCUMENTS

WO    WO/2007/021010    *    2/2007

\* cited by examiner

*Primary Examiner* — Michael Peffley
*Assistant Examiner* — Samantha Good
(74) *Attorney, Agent, or Firm* — Gael Diane Tisack, Esq.; Darryl Newell; MacMillan, Sobanski & Todd, LLC

(57) ABSTRACT

A cutter for a blood vessel tissue harvesting instrument is disposed at the distal end of an insertion member. A cutter body projecting from the distal end of the insertion member includes a slit that extends from the distal end toward a base edge. High-frequency electrodes are disposed along the sides of the slit. A feeding mechanism has rotating surfaces which are rotated as a result of being pressed by the tissue, and which feed the tissue toward the base edge of the slit. The rotating surfaces are provided by two rotary members disposed opposite each other along the two side edges of the slit, respectively, so that the first and second rotating surfaces move in a direction from the opening of the slit toward the base edge of the slit.

2 Claims, 7 Drawing Sheets

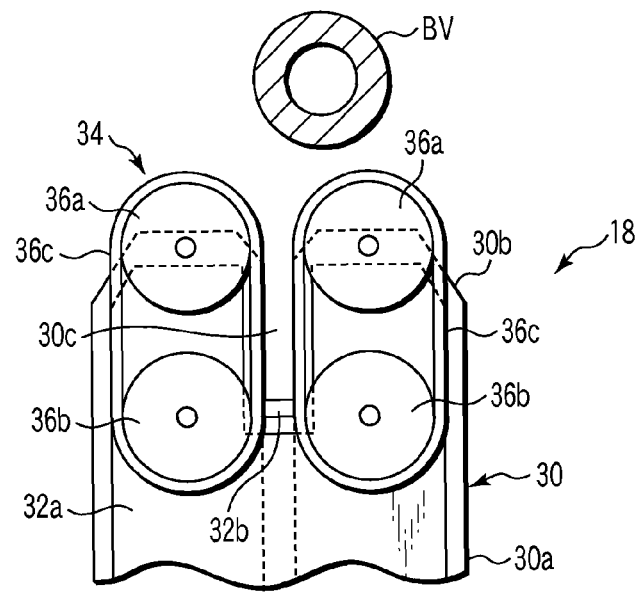
F I G. 3A
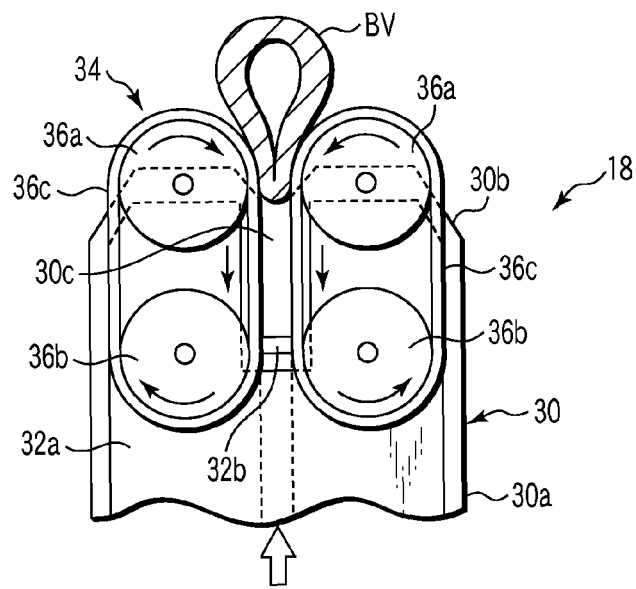
F I G. 3B
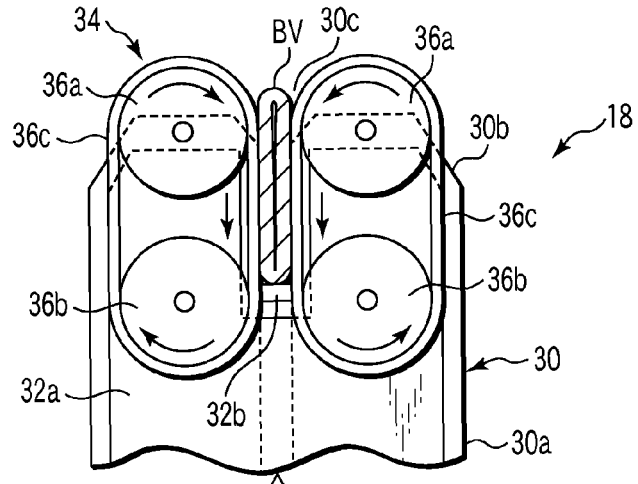
F I G. 3C

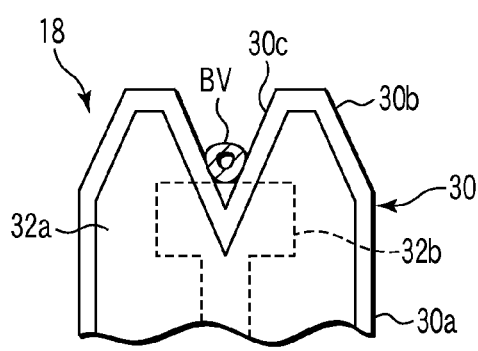
F I G. 6A
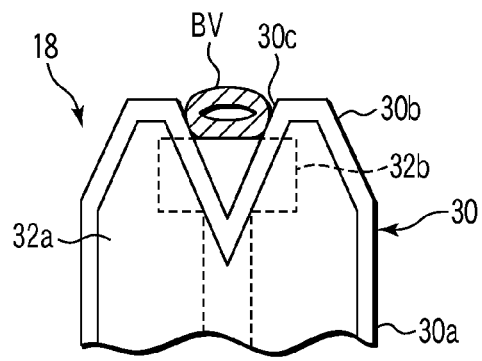
F I G. 6B
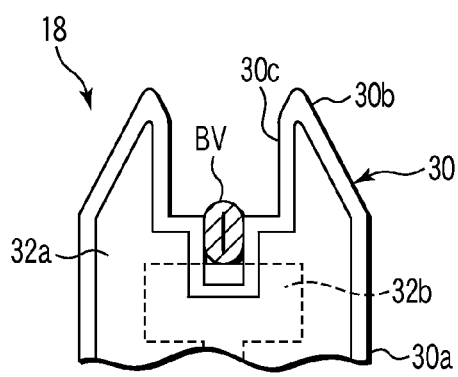
F I G. 7A
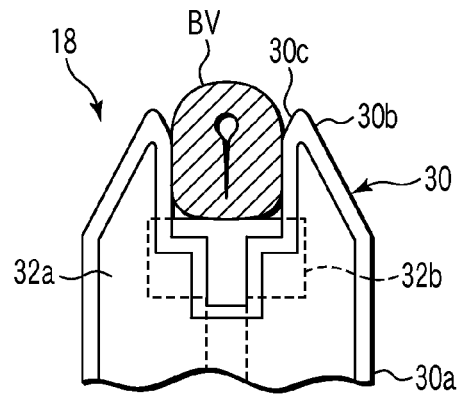
F I G. 7B
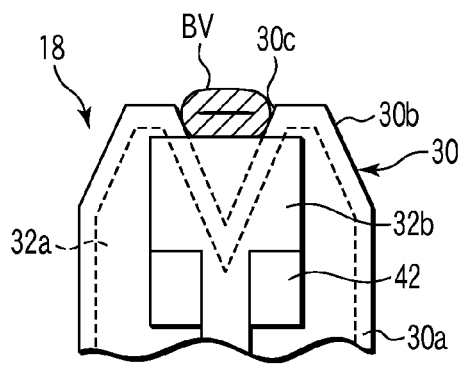
F I G. 8A
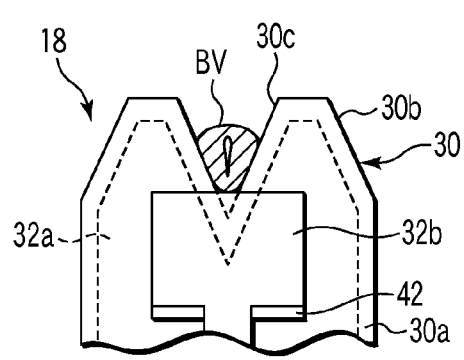
F I G. 8B

BODY TISSUE INCISION APPARATUS

CROSS REFERENCE TO RELATED APPLICATIONS

Not Applicable.

STATEMENT REGARDING FEDERALLY SPONSORED RESEARCH

Not Applicable.

BACKGROUND OF INVENTION

The present invention relates to an endoscopic instrument used to harvest body tissue such as a saphenous vein or other blood vessels for use in surgery to graft a harvested vessel into another site within a body, such as in a coronary bypass.

An instrument used to harvest blood vessels is known from Japanese Unexamined Patent Application Publication 2006-000485 (which is priority for U.S. patent application publication 2006/0206112A1). This conventional body tissue harvesting instrument is used in order to dissect veins from surrounding tissue and then to sever and remove the veins from inside the human body.

For example, in coronary bypass operations on blood vessels surrounding the heart, after the diseased (i.e., occluded) part of the blood vessels is identified, a portion of vein harvested from the patient's leg is used to create an alternate pathway for blood to perfuse the artery distally of the diseased vessel, thus making a bypass. When harvesting veins from a leg of the human body, it is frequently the case that a portion of the saphenous vein extending along the leg between the groin and the ankle is harvested.

The work of harvesting this portion of vein is conducted as follows. First, with the patient under general anesthesia, a skin incision followed by blunt dissection at the incision site is performed in the knee area of the leg. Next, a trocar is set in this opening and an elongated dissector (which is a blood-vessel dissecting instrument for separating the vessel from surrounding tissue) is inserted into the leg via the trocar. The insertion part of an endoscope is removably attached to the dissector, which is also provided with a channel for a fluid such as, for example, carbon dioxide gas. Under observation by this endoscope inserted near the knee, and sequentially working along the saphenous vein in two opposite directions (i.e., from the knee to the groin and then from the knee to the ankle), the aforementioned desired portion of the vein is separated and isolated from its surrounding tissue together with multiple small venous branches from the aforementioned desired vein portion. During this time, the aforementioned $CO_2$ fluid is emitted from the tip of the dissector, creating a cavity around the tip of the dissector inside the leg, thereby facilitating observation of the tip of the dissector by the endoscope.

Next, the dissector is removed from the leg interior, and in its place the surgeon or medical technician inserts an insertion member of a blood-vessel harvesting apparatus into the leg via the trocar. The insertion part of an endoscope is removably attached to the insertion member of the harvester, which is also provided with a channel for a fluid such as, for example, carbon dioxide gas. A blood-vessel holder is retractably provided at the tip of this insertion member, which is also provided with a retractable blood-vessel cutter. Operations including forward and backward movement of the blood-vessel holder at the aforementioned tip are made feasible by a blood-vessel holder manipulation member on a handle provided at the proximal end of the insertion member and which is exposed to outside space from the trocar. Operations including forward and backward movement of the blood-vessel cutter at the aforementioned tip are made feasible by a blood-vessel cutter manipulation member on the handle provided at the proximal end of the insertion member and which is exposed to outside space from the trocar.

While observing the aforementioned desired portion of vein via the endoscope, the blood-vessel holder manipulation member and/or the insertion member is manipulated by the surgeon or technician, and the aforementioned desired portion of vein is held by the blood-vessel holder. Furthermore, by manipulating at least one of blood-vessel holder manipulation member, insertion member, and blood-vessel cutter manipulation member, the aforementioned multiple small venous branches protruding from the desired portion of vein are sequentially cut by sequential use of the blood-vessel cutter, working from the knee to the groin and then from the knee to the ankle. The blood-vessel cutter is configured so as to simultaneously cut and cauterize blood vessels by means of application of a high-frequency current to generate extreme heat in a very localized area. During this time, the aforementioned fluid is emitted from the tip of the insertion member, creating a cavity around the tip of the insertion member inside the leg, and thereby facilitating observation of the tip of the insertion member by the endoscope.

When cutting of all of the aforementioned multiple small venous branches from the aforementioned desired portion of vein is completed, incisions are made at the surface of the leg in the respective regions of the groin and the ankle corresponding to the two ends of the aforementioned desired portion of vein in order to expose the two ends of the aforementioned desired portion of vein. Next, the two exposed ends of the aforementioned desired portion of vein are ligated, after which the two ends of the aforementioned desired portion of vein are cut on the inner side of the ligature position. The incisions in the groin and the ankle are then closed with, for example, adhesive plaster or the like. The aforementioned desired portion of vein whose two ends have been cut is extracted from the central opening in the knee, and this opening is finally closed with, for example, suturing adhesive plaster or the like.

The desired portion of vein harvested in this manner undergoes a check for the existence of perforations or lesions in the vascular wall, after which the portions free of perforations and lesions in the vascular wall are used in the aforementioned bypass operation.

The blood-vessel cutter of the conventional elongate body tissue harvesting instrument disclosed by Japanese Unexamined Patent Application Publication 2006-000485 contains a cutter which possesses a slit whose tip opens in a V-shape, with two electrodes disposed along the two side edges of the slit at the base end of the slit and the outer surface of the cutter. Here, the blood vessels captured in the tip of the slit which is opened in a V-shape are flattened by the slit while being moved to the base end of the slit, and in this state are burnt through by the high-frequency current which flows between the aforementioned two electrodes, whereby the cut portion is clotted (i.e., cauterized).

With respect to body tissue harvesting instruments for use in narrow places inside the body, there is constant demand for the ability to conduct more precise harvesting of body tissue in a shorter time, and with simpler operations.

SUMMARY OF INVENTION

The body tissue harvesting instrument according to one aspect of the present invention is provided with an insertion member which has a tip and a proximal end part wherein the tip is inserted first into the body and a cutter which is provided at the tip of the insertion member and which severs tissue inside the body. Furthermore, the cutter includes a cutter body having a proximal end part held at the tip of the insertion member, a projection which projects from the tip of the insertion member, and a slit which extends from the projection toward the proximal end part. A first high-frequency electrode is disposed along the two side edges of the slit on the outer surface of the cutter body. A second high-frequency electrode is disposed at the base end of the slit in the cutter body. A feeding mechanism is arranged on both sides of the distal end of the slit in the projection of the cutter body which is rotated as a result of being pressed by the aforementioned tissue and feeds the aforementioned tissue toward the interior of the slit.

The body tissue harvesting instrument according to another aspect of the present invention is provided with an insertion member which has a distal end and a proximal end part wherein the distal end is inserted first into the body and a cutter which is provided at the distal end of the insertion member and which severs tissue inside the body. Furthermore, the cutter includes a cutter body having a proximal end part held at the distal end of the insertion member, a projection which projects from the distal end of the insertion member, and a slit which extends from the projection toward the proximal end part. A first high-frequency electrode is disposed along the two side edges of the slit on the outer surface of the cutter body. A second high-frequency electrode is disposed at the base end of the slit in the cutter body. The parts located on both sides of the distal end of the slit in the projection of the cutter body mutually separate in the thickness direction of the slit which crosses both the extension direction and width direction of the slit.

The body tissue harvesting instrument according to yet another aspect of the present invention is provided with an insertion member which has a distal end and a proximal end wherein the distal end is inserted first into the body and a cutter which is provided at the distal end of the insertion member and which severs tissue inside the body. Furthermore, the cutter includes a cutter body which includes a proximal end part held at the distal end of the insertion member, a projection which projects from the distal end of the insertion member, and a slit which extends from the projection toward the proximal end part. A first high-frequency electrode is disposed along the two side edges of the slit on the outer surface of the cutter body. A second high-frequency electrode is capable of moving between the base end and distal end of the slit in the cutter body. Furthermore, the width of the distal end of the slit is set wider than the width of the base end of the slit.

The elongate body tissue harvesting instrument according to yet another aspect of the present invention is provided with an insertion member which has a distal end and a proximal end part wherein the distal end is inserted first into the body. A tissue holder is provided at the distal end of the insertion member which holds tissue inside the body so that it is capable of freely moving along the aforementioned tissue. A cutter is provided at the distal end of the insertion member which severs the aforementioned tissue held by the tissue holder. The tissue holder and cutter at the distal end of the insertion member mutually separate in a first crosswise direction which crosses a longitudinal center line connecting the distal end and the proximal end of the insertion member. Furthermore, the tissue holder includes a tissue holding frame which has a distal end part which projects from the distal end of the insertion member and which is far from the distal end of the insertion member. A proximal end part is closer to the distal end of the insertion member than the distal end part; and two arms extend in a second crosswise direction that crosses both the aforementioned longitudinal center line and the aforementioned first crosswise direction at both the distal end part and proximal end part, and which face each other in the direction along the aforementioned longitudinal center line. The two arms of the tissue holding frame mutually diverge in the first crosswise direction.

BRIEF DESCRIPTION OF DRAWINGS

The accompanying drawings, which are incorporated in and constitute part of the specification, illustrate embodiments of the invention, and together with the general description given above and the detailed description of the embodiments given below, serve to explain the principles of the invention.

FIG. 3A, FIG. 3B, and FIG. 3C are schematic plan views which sequentially show the procedure whereby a second embodiment of the cutter used in the body tissue harvesting instrument shown in FIG. 1 presses against in vivo body tissue (in this case, a vein in the leg of a human body), and severs the aforementioned body tissue.

FIG. 6A is a schematic plan view of a first state of use of a fourth embodiment of the cutter used in the body tissue harvesting instrument illustrated in FIG. 1.

FIG. 6B is a schematic plan view of a second state of use of the fourth embodiment of the cutter illustrated in FIG. 6A.

FIG. 7A is a schematic plan view of a first state of use of a fifth embodiment of the cutter used in the body tissue harvesting instrument illustrated in FIG. 1.

FIG. 7B is a schematic plan view of a second state of use of the fifth embodiment of the cutter illustrated in FIG. 7A.

FIG. 8A is a schematic plan view of a first state of use of a sixth embodiment of the cutter used in the body tissue harvesting instrument illustrated in FIG. 1.

FIG. 8B is a schematic plan view of a second state of use of the sixth embodiment of the cutter illustrated in FIG. 8A.

DETAILED DESCRIPTION OF PREFERRED EMBODIMENTS

Figure 1:
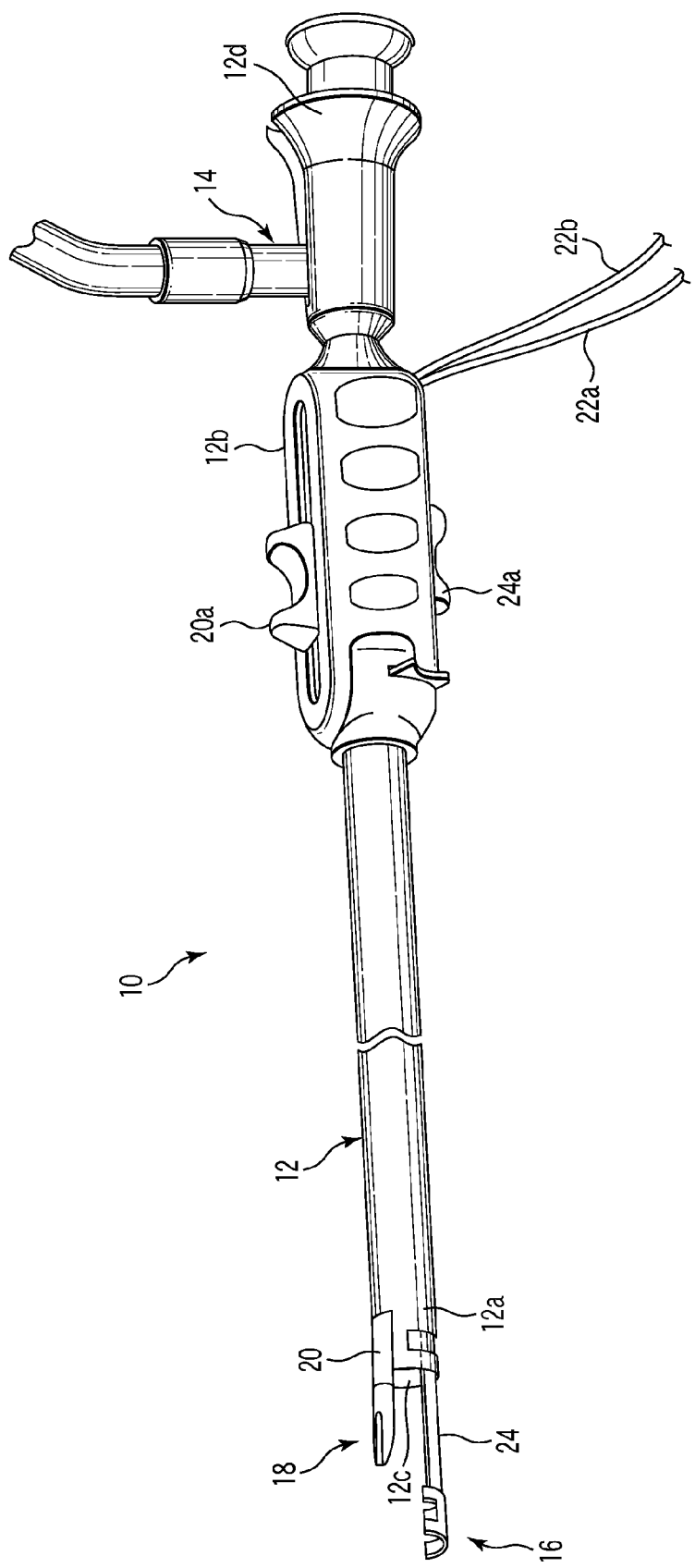
FIG. 1 is an oblique view which schematically shows the external appearance of the entirety of the body tissue harvesting instrument according to an embodiment of the present invention.

First, the overall configuration of a body tissue harvesting instrument 10 according to one embodiment of the present invention is described with reference to FIG. 1. The elongate body tissue harvesting instrument 10 is provided with an insertion member 12 which has a distal end 12a and proximal end part 12b where the distal end 12a is inserted first into the body. The insertion member 12 has a central aperture 12c which extends from the proximal end part 12b to the distal end 12a. An endoscope holder 12d which communicates with the central aperture 12c is set in the proximal end part 12b. In the central aperture 12c, an endoscope insertion part is provided which allows insertion of an endoscope 14 from the endoscope holder 12d to the distal end 12a. The endoscope 14 inserted into the endoscope insertion part of the central aperture 12c is removably held by the endoscope holder 12d. The tip of the endoscope 14 is disposed at the distal end 12a in the central aperture 12c of the insertion member 12. A monitor television which is not illustrated in the drawing is connected to the proximal end of the endoscope 14. Accordingly, the images captured via the observation window arranged at the foremost part of the tip of the endoscope 14 (that is, images of the tissue inside the body facing the distal end 12a of the insertion member 12) can be projected and observed on the screen of the aforementioned monitor television.

At the distal end 12a of the insertion member 12, a tissue holder 16 is provided which holds the tissue inside the body (as mentioned above, a vein inside the leg of a human body) and which is capable of freely moving along the aforementioned tissue. The distal end 12a of the insertion member 12 is further provided with a cutter 18 which severs the collateral venous branches which are part of the aforementioned tissue held by the tissue holder 16. The tissue holder 16 and cutter 18 at the distal end 12a of the insertion member 12 mutually separate in a first crosswise direction (e.g., the diametric direction of the insertion member 12) which crosses a longitudinal center line connecting the distal end 12a and proximal end part 12b of the insertion member 12. The cutter 18 is attached to the tip of a cutter manipulation member 20 which extends inside the insertion member 12 from the proximal end part 12b to the distal end 12a so as to be capable of freely moving forward or backward in the aforementioned longitudinal direction. The proximal end part of the cutter manipulation member 20 is fixed to a cutter manipulation slider 20a which is exposed on the outer surface of the proximal end part 12b of the insertion member 12 so as to be capable of freely moving forward or backward in the aforementioned longitudinal direction.

As described in detail below, the cutter 18 has two high-frequency electrodes, which are not illustrated in FIG. 1. Two conductive wires for the two high-frequency electrodes extend inside the insertion member 12 from the distal end 12a to the proximal end part 12b along the cutter manipulation member 20. The aforementioned two conductive wires 22a and 22b extend from the proximal end part 12b to the outside, where they connect to a conventional high-frequency power source, which is not illustrated in FIG. 1.

The configuration of the tissue holder 16 is described in detail below, but the aforementioned configuration for the most part extends from the distal end 12a of the insertion member 12, and is fixed to the distal end 12a, while a portion of the aforementioned configuration projects from the distal end 12a of the insertion member 12, and attaches to the tip of a tissue holder switching manipulation member 24. The tissue holder switching manipulation member 24 extends inside the insertion member 12 from the distal end 12a to the proximal end part 12b so as to be capable of freely moving forward or backward in the aforementioned longitudinal direction, and the proximal end part of the tissue holder switching manipulation member 24 is fixed to a tissue holder switching slider 24a which is exposed on the outer surface of the proximal end part 12b of the insertion member 12 so as to be capable of freely moving forward or backward in the aforementioned longitudinal direction.

At least one or the other of the tissue holder 16 and cutter 18 is capable of moving forward or backward along the longitudinal center line of the insertion member 12 relative to the distal end 12a of the insertion member 12 between a facing position where the tissue holder 16 and cutter 18 face each other, and a facing separation position where the cutter 18 is brought closer to the distal end 12a of the insertion member 12 than the tissue holder 16. In this embodiment, as stated above, the cutter 18 is capable of moving forward or backward between the facing position and the facing separation position by moving forward or backward along the longitudinal center line of the insertion member 12 relative to the distal end 12a of the insertion member 12. In FIG. 1, the cutter 18 is arranged at the facing separation position relative to the tissue holder 16.

By manipulating the cutter manipulation slider 20a, and by distancing the cutter 18 at the facing separation position of FIG. 1 from the distal end 12a of the insertion member 12, it is possible to dispose the cutter 18 in the facing position relative to the tissue holder 16. Next, a description of the configuration and operation of a first embodiment of the cutter 18 used in the body tissue harvesting instrument 10 illustrated in FIG. 1 is given, with reference to FIG. 2A through FIG. 2C.

The first embodiment of configuration of the cutter 18 is provided with a cutter body 30 of non-conductive material which includes a proximal end part 30a held in the distal end 12a of the insertion member 12 by attachment to the tip of the cutter manipulation member 20 located at the distal end 12a of the insertion member 12, and a projection 30b which projects from the distal end 12a of the insertion member 12. The cutter body 30 further includes a slit 30c which opens in the projection 30b and which extends from the projection 30b toward the proximal end part 30a.

A first high-frequency electrode 32a is disposed along the two side edges of the slit 30c on the outer surface of the cutter body 30, and a second high-frequency electrode 32b is disposed at the inner end of the slit 30c in the cutter body 30. As stated above with reference to FIG. 1, the first high-frequency electrode 32a and second high-frequency electrode 32b are connected to the aforementioned conventional high-frequency power source (not illustrated in FIG. 1) by the two conductive wires 22a and 22b which extend inside the insertion member 12 from the distal end 12a to the proximal end part 12b along the cutter manipulation member 20.

At the distal end of the slit 30c in the projection 30b of the cutter body 30, a feeding mechanism 34 is provided which rotates as a result of being pressed by a portion of the desired tissue inside the body (e.g., a venous collateral branch which is part of a desired vein inside the leg of a human body), and which feeds elongate tissue toward the interior of the slit 30c.

In further detail, with respect to this first embodiment of the cutter 18, the feeding mechanism 34 includes two rotary members 34a which rotate so that the parts which are arranged opposite each other on the two sides of the distal end of the slit 30c in the projection 30b of the cutter body 30 move in a direction from the distal end toward the base end of the slit 30c. On the respective circumferential faces of the two rotary members 34a, a conventional slippage stopper is arranged so as to minimize as much as possible slippage of the desired portion of tissue inside the body (e.g., venous collateral branch which is part of a desired vein inside the leg of a human body) which makes contact with these circumferential faces. As stated above with reference to FIG. 1, the distal end 12a of the insertion member 12 associated with the cutter body 30 of the first embodiment of the cutter 18 is oriented toward the desired tissue site inside the body (e.g., the desired vein inside the leg of a human body) under observation by the endoscope 14. Subsequently, the tissue holder switching slider 24a at the proximal end part 12b of the insertion member 12 is manipulated, and the aforementioned desired tissue site inside the body is removably held by the tissue holder 16 (see FIG. 1).

Figure 2A:
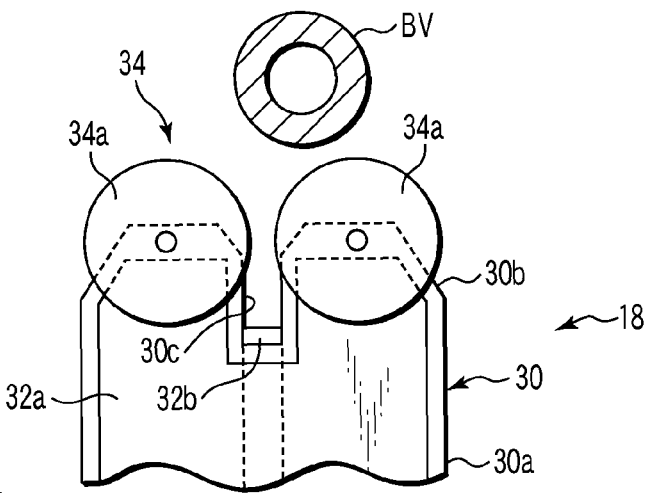
FIG. 2A, FIG. 2B, and FIG. 2C are schematic plan views which sequentially show the procedure whereby a first embodiment of the cutter used in the body tissue harvesting instrument shown in FIG. 1 presses against in vivo body tissue (in this case, a vein in the leg of a human body), and severs the aforementioned body tissue.

Next, the proximal end part 12b of the insertion member 12 is manipulated so that the tissue holder 16 is moved along the aforementioned desired tissue site inside the body (e.g., the desired vein inside the leg of a human body). As a result, as shown in FIG. 2A, the distal end of the slit 30c of the projection 30b of the cutter body 30 of the first embodiment of the cutter 18 is made to approach a portion of the desired tissue site BV inside the body (e.g., a collateral branch of the aforementioned desired vein inside a leg).

Figure 2B:
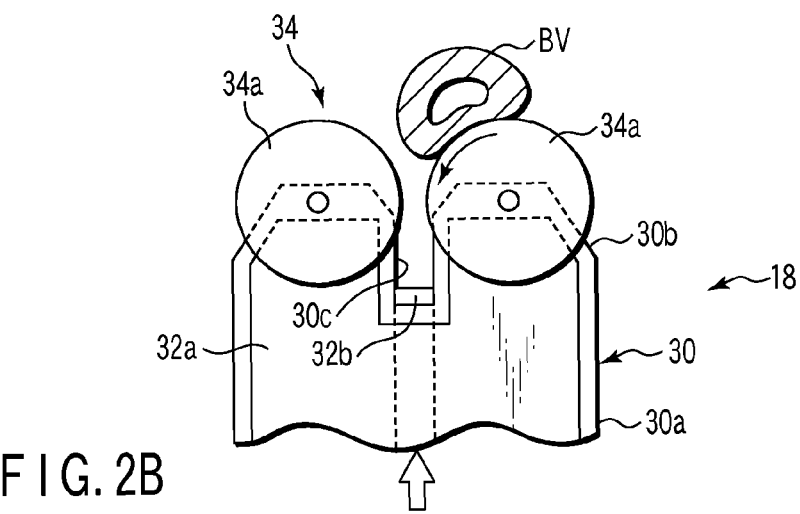

Next, as shown in FIG. 2B, the cutter manipulation slider 20a of the cutter manipulation member 20 is advanced, and at least one of the circumferential faces of the two rotary members 34a of the feeding mechanism 34 of the projection 30b of the cutter body 30 presses against a portion of the aforementioned desired tissue site BV (e.g., the collateral branch of the aforementioned desired vein inside a leg). As a result, at least one of the two rotary members 34a rotates so that the portion of the aforementioned desired tissue site BV moves in the direction from the distal end toward the base end of the slit 30c.

Figure 2C:
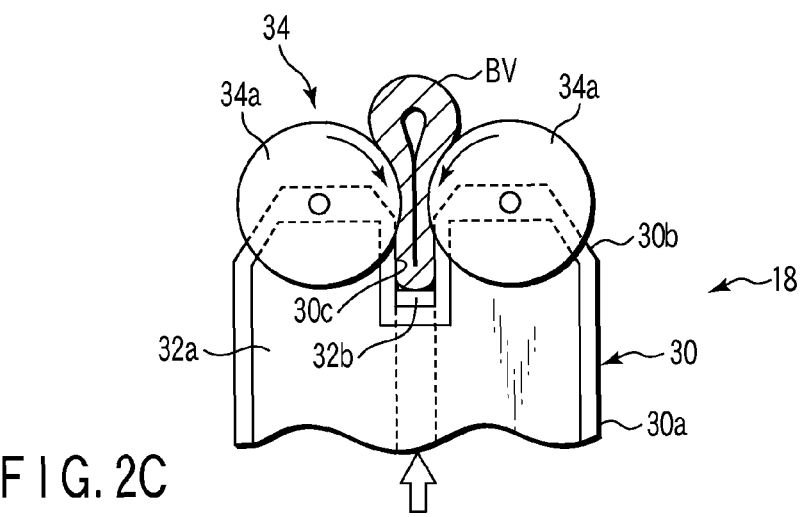

When the cutter manipulation slider 20a of the cutter manipulation member 20 is further pressed, the portion of the aforementioned desired tissue site BV contacts the portion of the feeding mechanism 34 where the two circumferential faces of the two rotary members 34a face each other at the distal end of the slit 30c. As a result, as shown in FIG. 2C, the portion of the aforementioned desired tissue site BV is pressed and flattened by the two circumferential faces of the two rotary members 34a, and is pressed against the second high-frequency electrode 32b at the base end of the slit 30c.

High-frequency current flows from the aforementioned high-frequency power source which is not illustrated in the drawings to the first high-frequency electrode 32a disposed along the two side edges of the slit 30c on the outer surface of the cutter body 30 and the second high-frequency electrode 32b disposed at the base end of the slit 30c via the two conductive wires 22a and 22b illustrated in FIG. 1, and during this time the cutter manipulation slider 20a of the cutter manipulation member 20 is further pressed. As a result, a portion of the aforementioned desired tissue site BV flattened in the slit 30c is severed by the high-frequency current which flows between the first high-frequency electrode 32a and second high-frequency electrode 32b, and the severed portion is clotted.

Next, a description of the configuration and operation of a second embodiment of the cutter 18 used in the body tissue harvesting instrument 10 illustrated in FIG. 1 is given, with reference to FIG. 3A through FIG. 3C. Most of the configuration of the second embodiment of the cutter 18 is identical to most of the configuration of the first embodiment of the cutter 18, which was described above with reference to FIG. 2A through FIG. 2C. Components of the second embodiment of the cutter 18 which are identical to the configuration of the first embodiment of the cutter 18 are given reference codes identical to the reference codes assigned to the corresponding components in the first embodiment of the cutter 18, and detailed description of these components is omitted.

The second embodiment of the cutter 18 differs from the first embodiment of the cutter 18 with respect to the configuration of the feeding mechanism 34. Specifically, the feeding mechanism 34 includes two rotary members 36a which rotate so that the parts which are disposed opposite each other on both sides of the distal end of the slit 30c in the projection 30b of the cutter body 30 move in the direction from the distal end toward the base end of the slit 30c. The feeding mechanism 34 further includes two subsidiary rotary members 36b which rotate so that the parts which are disposed opposite each other on both sides of the base end of the slit 30c at the base end part 30a of the cutter body 30 move in the direction from the distal end toward the base end of the slit 30c. Two gear members or belts 36c engage with each of the aforementioned two rotary members 36a and each of the aforementioned two subsidiary rotary members 36b, respectively, and they move the parts which extend opposite each other along the two side edges of the slit 30c in the direction from the distal end toward the base end of the slit 30c in conjunction with the rotation of each of the two rotary members 36a and each of the two subsidiary rotary members 36b. On the respective circumferential faces of the two rotary members 36a and the two subsidiary rotary members 36b, a conventional slippage stopper is arranged so as to minimize as much as possible slippage relative to the gear members 36c which engage with these. Each of the two gear members 36c are flexible, and a conventional slippage stopper is arranged so as to minimize slippage as much as possible relative to the portion of desired tissue inside the body (e.g., the venous branches which are part of a desired vein inside a leg of the human body) which contacts these.

As stated above with reference to FIG. 1, the distal end 12a of the insertion member 12 associated with the cutter body 30 of the second embodiment of the cutter 18 is oriented toward the desired tissue site inside the body (e.g., the desired vein inside a leg of the human body) under the observation of the endoscope 14. Subsequently, the tissue holder switching slider 24a of the proximal end part 12b of the insertion member 12 is manipulated, and the aforementioned desired tissue site inside the body is removably held by the tissue holder 16 (see FIG. 1).

Next, the proximal end part 12b of the insertion member 12 inside the body (e.g., inside a leg of the human body) is manipulated so that the tissue holder 16 is moved along the desired site of the aforementioned elongate tissue inside the body (e.g., the desired vein inside a leg of the human body). As a result, as shown in FIG. 3A, the distal end of the slit 30c of the projection 30b of the cutter body 30 of the second embodiment of the cutter 18 is made to approach the desired tissue site inside the body BV.

Next, when the cutter manipulation slider 20a of the cutter manipulation member 20 is advanced, and when the outer surface of the gear member 36c on at least one of the circumferential faces of the two rotary members 36a of the feeding mechanism 34 of the projection 30b of the cutter body 30 presses against a portion of the aforementioned desired tissue site BV, at least one of the aforementioned gear members 36c moves so that the aforementioned portion of the desired tissue site BV is fed in the direction from the distal end toward the base end of the slit 30c, while at least one of the aforementioned rotary members 36a and at least one of the subsidiary rotary members 36b corresponding thereto rotate in the direction from the distal end toward the base end of the slit 30c.

When the cutter manipulation slider 20*a* of the cutter manipulation member 20 is further pressed, as shown in FIG. 3B, the aforementioned portion of the desired tissue site BV (e.g., venous branch of the aforementioned desired vein inside a leg) is squeezed by the outer surfaces of the two gear members 36*c* on the two circumferential faces of the two rotary members 36*a* of the feeding mechanism 34 at the distal end of the slit 30*c*. Subsequently, the two gear members 36*c* move so that the aforementioned portion of the desired tissue site BV is fed toward the interior of the slit 30*c* by the parts which extend opposite each other along the two side edges of the slit 30*c*.

As a result, as shown in FIG. 3C, the aforementioned portion of the desired tissue site BV which has been pressed and flattened by the parts which extend opposite each other along the two side edges of the slit 30*c* in the two gear members 36*c* are pressed against the second high-frequency electrode 32*b* at the base end of the slit 30*c*. High-frequency current flows from the aforementioned high-frequency power source (not shown) to the first high-frequency electrode 32*a* disposed along the two side edges of the slit 30*c* on the outer surface of the cutter body 30 and the second high-frequency electrode 32*b* at the base end of the slit 30*c* via the two conductive wires 22*a* and 22*b* illustrated in FIG. 1, and during this time the cutter manipulation slider 20*a* of the cutter manipulation member 20 is further pressed. As a result, the aforementioned portion of the desired tissue site BV which has been flattened in the slit 30*c* is severed by the high-frequency current which flows between the first high-frequency electrode 32*a* and second high-frequency electrode 32*b*, and the severed portion is clotted.

Figure 4A:
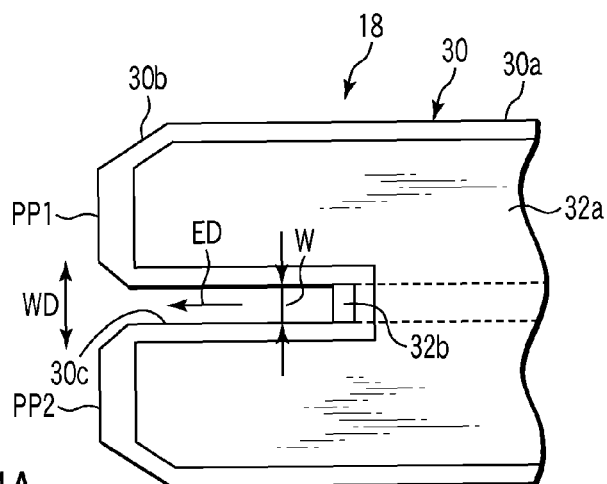
FIG. 4A is a schematic plan view of a third embodiment of the cutter used in the body tissue harvesting instrument illustrated in FIG. 1.
Figure 4B:
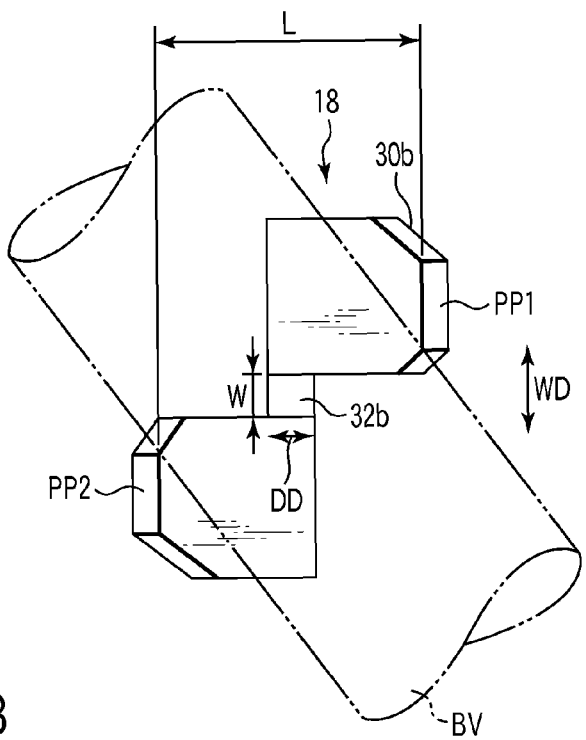
FIG. 4B is a schematic frontal view of the third embodiment of the cutter illustrated in FIG. 4A.
Figure 4C:
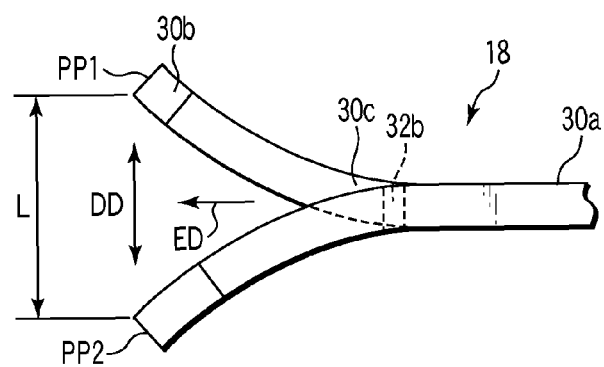
FIG. 4C is a schematic side view of the third embodiment of the cutter illustrated in FIG. 4A.

Next, a description of the configuration and operation of a third embodiment of the cutter 18 used in the body tissue harvesting instrument 10 illustrated in FIG. 1 is given, with reference to FIG. 4A through FIG. 4C.

Most of the configuration of the third embodiment of the cutter 18 is identical to most of the configuration of the first embodiment of the cutter 18 which was described above with reference to FIG. 2A through FIG. 2C. Components of the third embodiment of the cutter 18 which are identical to the configuration of the first embodiment of the cutter 18 are given reference codes identical to the reference codes assigned to the corresponding components in the first embodiment of the cutter 18, and detailed description of these components is omitted.

The third embodiment of the cutter 18 differs from the first embodiment of the cutter 18 in that it is not provided with the feeding mechanism 34, and instead, parts PP1 and PP2 located on both sides of the distal end of the slit 30*c* in the projection 30*b* of the cutter body 30 mutually separate in the thickness direction DD of the slit which crosses both the extension direction ED and width direction WD of the slit 30*c*.

In further detail, in the third embodiment of this cutter 18, the distance L with which parts PP1 and PP2—which are located on both sides of the distal end of the slit 30*c* in the projection 30*b* of the cutter body 30—mutually separate in the thickness direction DD of the slit which crosses both the extension direction ED and width direction WD of the slit 30*c* is larger than the width W at the base end of the slit 30*c*.

As shown by the double-dot-and-dash line in FIG. 4B, if constituted in this way, and if there is a portion of the aforementioned desired tissue site BV with a diameter smaller than the aforementioned distance L, it can be easily introduced into the distal end of the slit 30*c* by the parts PP1 and PP2 which are located on both sides of the distal end of the slit 30*c* in the projection 30*b* of the cutter body 30. Subsequently, when the cutter manipulation slider 20*a* of the cutter manipulation member 20 is further pressed, the portion of the aforementioned desired tissue site BV which has been introduced is flattened and pressed by the movement toward the interior of the slit 30*c* and by the two side faces of the slit 30*c* so that it approaches the aforementioned width W.

The aforementioned portion of the desired tissue site BV which has been flattened is then pressed against the second high-frequency electrode 32*b* at the base end of the slit 30*c*. High-frequency current flows under manual control of the surgeon or technician to the first high-frequency electrode 32*a* located along the two sides of the slit 30*c* on the outer surface of the cutter body 30 and to the second high-frequency electrode 32*b* at the base end of the slit 30*c* via the two conductive wires 22*a* and 22*b* illustrated in FIG. 1 from the aforementioned high-frequency power source (not shown), and during this time the cutter manipulation slider 20*a* of the cutter manipulation member 20 is further pressed. As a result, the aforementioned portion of the desired tissue site BV which is flattened in the slit 30*c* is severed by the high-frequency current which flows between the first high-frequency electrode 32*a* and second high-frequency electrode 32*b*, and the severed portion is clotted.

Figure 5A:
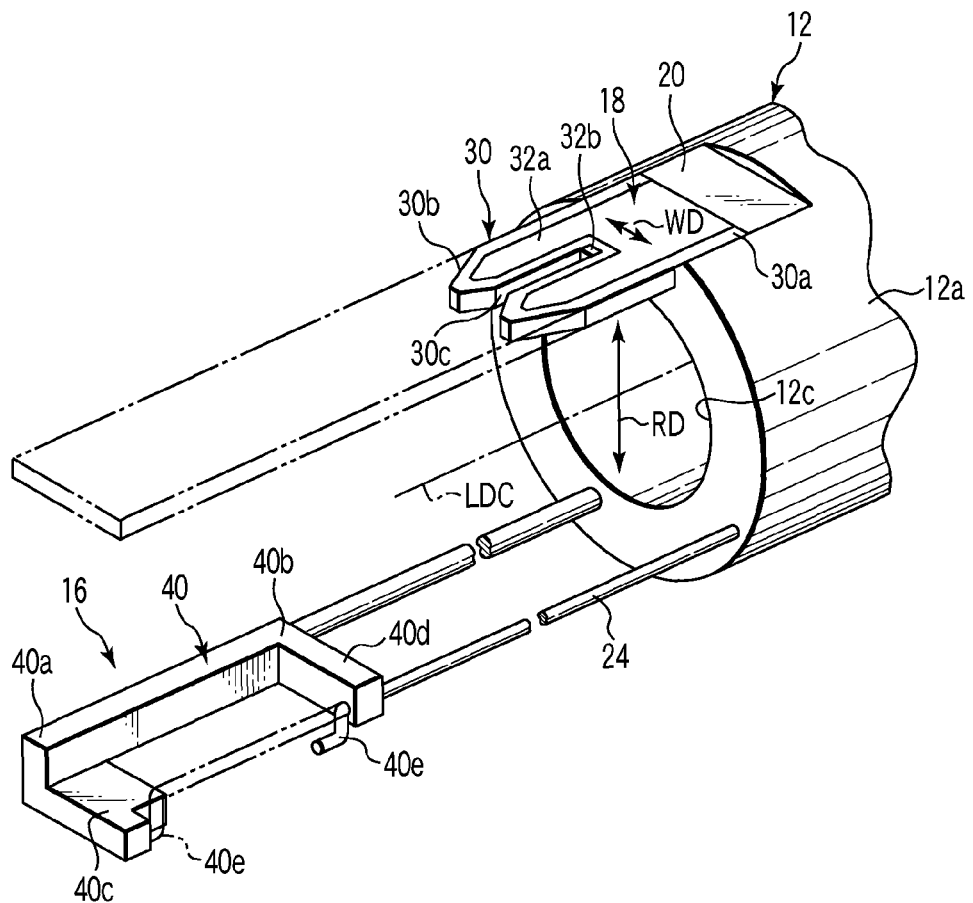
FIG. 5A is a schematic oblique view of one embodiment of the tissue holder used in the body tissue harvesting instrument shown in FIG. 1.
Figure 5B:
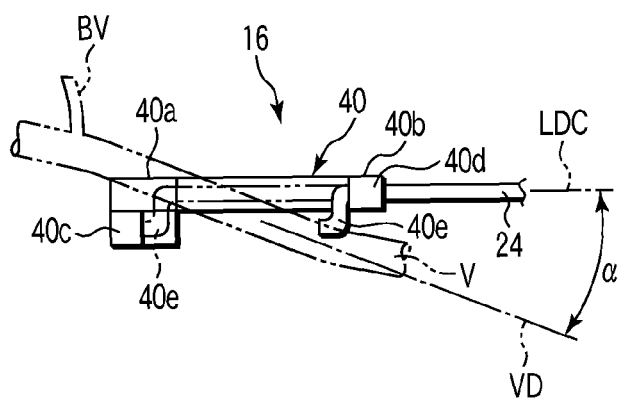
FIG. 5B is a schematic side view of the tissue holder illustrated in FIG. 5A.

Next, a description of the configuration and operation of a first embodiment of the tissue holder 16 used in the body tissue harvesting instrument 10 illustrated in FIG. 1 is given, with reference to FIG. 5A and FIG. 5B.

The tissue holder 16 includes a tissue holding frame 40 which projects from the distal end 12*a* of the insertion member 12 and which is fixed to the distal end 12*a*. The tissue holding frame 40 includes a distal end part 40*a* which is far from the distal end 12*a* of the insertion member 12; a proximal end part 40*b* which is closer to the distal end 12*a* of the insertion member 12 than the distal end part 40*a*; and two arms 40*c* and 40*d* which extend in a second crosswise direction (e.g., the width direction WD of the slit 30*c* of the cutter body 30 of the cutter 18) that crosses—at both the distal end part 40*a* and proximal end part 40*b*—both a longitudinal center line LDC of the insertion member 12 and a first crosswise direction (e.g., the diametric direction RD of the insertion member 12) that crosses this longitudinal center line LDC, and which face each other in the direction along the aforementioned longitudinal center line LDC. The two arms 40*c* and 40*d* of the tissue holding frame 40 mutually diverge in the first crosswise direction.

The tissue holder 16 further includes a frame switching member 40*e* which projects from the distal end 12*a* of the insertion member 12, and which is able to move forward and backward along the aforementioned longitudinal center line LDC between a closed position where the gap between the mutually extended ends of the two arms 40*c* and 40*d* of the tissue holding frame 40 is closed and an open position where the aforementioned gap is open.

In further detail, in this embodiment, the tip of the tissue holder switching manipulation member 24 is held by the aforementioned arm 40*d* of the proximal end part in the tissue holding frame 40 so as to be capable of moving forward or backward along the aforementioned longitudinal center line LDC. At this tip of the tissue holder switching manipulation member 24, the part which projects into the gap between the arm 40*c* of the distal end part and the arm 40*d* of the proximal end part of the tissue holding frame 40 constitutes the frame switching member 40*e*. The frame switching member 40*e* projects from the distal end 12*a* of the insertion member 12 by being integrally formed with (attached to) the tip of the tissue holder switching manipulation member 24.

In FIG. 5A and FIG. 5B, the closed position of the frame switching member 40e is illustrated by a double-dotted-and-dashed line, and the open position is illustrated by a solid line. With respect to the cutter 18 at the distal end 12a of the insertion member 12 in FIG. 5A, the facing position which faces the tissue holding frame 40 of the tissue holder 16 is illustrated by a double-dotted-and-dashed line, while the facing separation position which is closer to the distal end 12a of the insertion member 12 than the tissue holding frame 40 is illustrated by a solid line.

In order to have the tissue holder 16 hold the aforementioned desired tissue site inside the body (e.g., a desired vein inside a leg of the human body), the distal end 12a of the insertion member 12 associated with the cutter body 30 of the cutter 18 is oriented toward the desired tissue site inside the body (e.g., a desired vein inside a leg of the human body) under observation by the endoscope 14, as was previously described with reference to FIG. 1. Subsequently, the tissue holder switching slider 24a (see FIG. 1) at the proximal end part 12b of the insertion member 12 is manipulated, the frame switching member 40e of the tissue holder 16 is moved to the open position, the proximal end part 12b of the insertion member 12 is further manipulated, and the aforementioned desired tissue site inside the body (e.g., a desired vein inside a leg of the human body) V is made to enter between the two arms 40c and 40d of the frame switching member 40e as shown in FIG. 5B via the gap between the extended ends of the two arms 40c and 40d of the frame switching member 40e. Finally, the tissue holder switching slider 24a at the proximal end part 12b of the insertion member 12 is again manipulated, and the frame switching member 40e of the tissue holder 16 is moved to the closed position, with the result that the aforementioned desired tissue site inside the body V is removably held by the tissue holder 16.

As shown in FIG. 5B, the tissue holding frame 40 of the tissue holder 16 is in this state capable of relative movement along the aforementioned desired tissue site inside the body (e.g., a desired vein inside a leg of the human body). Moreover, as the two arms 40c and 40d of the tissue holding frame 40 mutually diverge in the first crosswise direction (e.g., the diametric direction RD of the insertion member 12) which crosses the longitudinal center line (LDC) of the insertion member 12, during the operation where the aforementioned desired tissue site inside the body (e.g., a desired vein inside a leg of the human body) V is made to enter between the two arms 40c and 40d of the frame switching member 40e as shown in FIG. 5B via the gap between the extended ends of the two arms 40c and 40d of the frame switching member 40e, it is possible to reduce the angle α established by the longitudinal center line LDC of the insertion member 12 relative to the longitudinal direction VD of the aforementioned desired tissue site inside the body (e.g., a desired vein inside a leg of the human body) V. That is, it is possible to have the aforementioned operation conducted in a state where the longitudinal center line LDC of the insertion member 12 has been brought closer to the longitudinal direction VD of the aforementioned desired tissue site inside the body (e.g., a desired vein inside a leg of the human body) V, and this facilitates the conduct of the aforementioned operation inside the body (e.g., inside a leg of the human body).

Next, the proximal end part 12b of the insertion member 12 inside the body (e.g., inside a leg of the human body) is manipulated so that the tissue holder 16 moves along the aforementioned desired tissue site inside the body (e.g., a desired vein inside a leg of the human body) V, and the distal end of the slit 30c of the projection 30b of the cutter body 30 of the cutter 18 is brought closer to a portion of the aforementioned desired tissue site V (e.g., venous collateral of the aforementioned desired vein inside a leg) where a collateral branch BV is located.

Next, the cutter manipulation slider 20a of the cutter manipulation member 20 (see FIG. 1) is advanced, and a portion of the aforementioned desired tissue site BV is introduced into the interior of the slit 30c of the projection 30b of the cutter body 30. During this time, the aforementioned portion of the desired tissue site BV is pressed and flattened by the two side edges of the slit 30c, and the aforementioned portion of the desired tissue site BV is pressed against the second high-frequency electrode 32b at the base end of the slit 30c. Furthermore, when high-frequency current flows from the aforementioned high-frequency power source to the first high-frequency electrode 32a disposed along the two side edges of the slit 30c on the outer surface of the cutter body 30 and the second high-frequency electrode 32b at the inner end of the slit 30c via the two conductive wires 22a and 22b illustrated in FIG. 1, the aforementioned portion of the desired tissue site BV which has been flattened is severed by the high-frequency current which flows between the first high-frequency electrode 32a and second high-frequency electrode 32b, and the severed portion is clotted.

Next, a description of the configuration and operation of a fourth embodiment of the cutter 18 used in the body tissue harvesting instrument 10 illustrated in FIG. 1 is given, with reference to FIG. 6A and FIG. 6B. Most of the configuration of the fourth embodiment of the cutter 18 is identical to most of the configuration of the first embodiment of the cutter 18 which was described above with reference to FIG. 2A through FIG. 2C. Components of the fourth embodiment of the cutter 18 which are identical to the configuration of the first embodiment of the cutter 18 are given reference codes identical to the reference codes assigned to the corresponding components in the first embodiment of the cutter 18, and detailed description of these components is omitted.

The fourth embodiment of the cutter 18 differs from the first embodiment of the cutter 18 in that it is not provided with the feeding mechanism 34, instead of which the width of the distal end of the slit 30c of the cutter body 30 is set larger than the width of the base end of the slit 30c, and the second high-frequency electrode 32b in the slit 30c moves freely between the base end and a position near the distal end of the slit 30c. In further detail, in this embodiment, the slit 30c has a triangular shape where the base end constitutes one apex, or it forms a V-shape where the width widens as one moves from the base end toward the distal end.

The movement of the second high-frequency electrode 32b in the aforementioned manner is conducted by manipulating the base end part of the second high-frequency electrode manipulation member (not shown) and which extends from the base end part 30b of the cutter body 30 in the insertion member 12 (see FIG. 1) to the proximal end part 12b of the insertion member 12 along the cutter manipulation member 20.

In this fourth embodiment of the cutter 18, if there is a portion of a desired tissue site inside the body of an organism BV which is capable of being introduced into the distal end of the triangular or V-shaped slit 30c, it is possible to press the second high-frequency electrode 32b against the outer circumferential face of the aforementioned portion of the desired tissue site BV which has been introduced into the distal end of the triangular or V-shaped slit 30c.

FIG. 6A shows a first condition where a portion of the aforementioned desired tissue site BV which has a diameter slightly larger than the width of the base end of the slit 30c has been introduced into the triangular or V-shaped slit 30c, and is pressed against the second high-frequency electrode 32b at the aforementioned base end. In this condition, while high-frequency current is flowing in the above-described manner to the first and second high-frequency electrodes 32a and 32b, if the cutter body 30 is pressed along with the second high-frequency electrode 32b toward the aforementioned portion of the desired tissue site of small diameter BV, the aforementioned portion of the desired tissue site of small diameter BV which has been flattened and pressed against the second high-frequency electrode 32b is severed by the high-frequency current which flows between the first high-frequency electrode 32a and second high-frequency electrode 32b, and the severed portion is clotted.

FIG. 6B shows a second condition where a portion of the aforementioned desired tissue site BV which has a diameter slightly smaller than the width of the distal end of the slit 30c has been introduced into the triangular or V-shaped slit 30c, and is held by the distal ends of the two side faces of the slit 30c, and where—if it is not possible to move any further toward the base end of the slit 30c—the base end of the aforementioned second high-frequency electrode manipulation member (not shown) is manipulated, the second high-frequency electrode 32b is moved from the base end toward the distal end of the slit 30c, and the second high-frequency electrode 32b is pressed against the outer circumferential face of the aforementioned portion of the desired tissue site of large diameter BV which is held.

In this condition, while high-frequency current is flowing in the above-described manner to the first and second high-frequency electrodes 32a and 32b, if the cutter body 30 is pressed along with the second high-frequency electrode 32b toward the aforementioned portion of the desired tissue site of large diameter BV, the aforementioned portion of the desired tissue site of large diameter BV which has been flattened and pressed against the second high-frequency electrode 32b is severed by the high-frequency current which flows between the first high-frequency electrode 32a and second high-frequency electrode 32b, and the severed portion is clotted.

Next, a description of the configuration and operation of a fifth embodiment of the cutter 18 used in the body tissue harvesting instrument 10 illustrated in FIG. 1 is given, with reference to FIG. 7A and FIG. 7B. Most of the configuration of the fifth embodiment of the cutter 18 is identical to most of the configuration of the first embodiment of the cutter 18 which was described above with reference to FIG. 2A through FIG. 2C. Components of the fifth embodiment of the cutter 18 which are identical to the configuration of the first embodiment of the cutter 18 are given reference codes identical to the reference codes assigned to the corresponding components in the first embodiment of the cutter 18, and detailed description of these components is omitted.

The fifth embodiment of the cutter 18 differs from the first embodiment of the cutter 18 in that it is not provided with the feeding mechanism 34, instead of which the width of the distal end of the slit 30c of the cutter body 30 is set larger than the width of the base end of the slit 30c, and the second high-frequency electrode 32b in the slit 30c moves freely between the base end and a position near the distal end of the slit 30c. In further detail, in this embodiment, the slit 30c has a shape where the width sequentially widens in a stepwise manner from the base end toward the distal end of the slit 30c, and the two side edges of the slit 30c have a wide part of fixed width which is arranged on the distal end side, and a narrow part of a fixed width narrower than the wide part which is arranged on the base end side.

The movement of the second high-frequency electrode 32b in the aforementioned manner is conducted by manipulating the base end part of the second high-frequency electrode manipulation member (not shown) and which extends from the base end part 30b of the cutter body 30 in the insertion member 12 (see FIG. 1) to the proximal end part 12b of the insertion member 12 along the cutter manipulation member 20. It is then possible to press the second high-frequency electrode 32b against the outer circumferential face of a portion of the desired tissue site of large diameter inside the body BV which is capable of being introduced into the wide part of large width on the distal end side of the slit 30c, and against the outer circumferential face of a portion of the desired tissue site of small diameter inside the body BV which is capable of being introduced into the narrow part of small width on the base end side of the slit 30c.

FIG. 7A shows a first condition where the aforementioned portion of the desired tissue site BV which has a diameter slightly larger than the aforementioned narrow part is introduced into and flattened by the narrow part on the base end side of the slit 30c, and is pressed against the second high-frequency electrode 32b in the narrow part on the base end side of the slit 30c. In this condition, while high-frequency current is flowing in the above-described manner to the first and second high-frequency electrodes 32a and 32b, if the cutter body 30 is pressed along with the second high-frequency electrode 32b toward the aforementioned portion of the desired tissue site of small diameter BV, the aforementioned portion of the desired tissue site of small diameter BV which has been flattened and pressed against the second high-frequency electrode 32b is severed by the high-frequency current which flows between the first high-frequency electrode 32a and second high-frequency electrode 32b, and the severed portion is clotted.

FIG. 7B shows a second condition where a portion of the aforementioned desired tissue site BV which has a diameter slightly larger than the aforementioned wide part has been introduced into and flattened by the wide part on the distal end side of the slit 30c, and where—if it is not possible to introduce it into the mouth of the narrow part on the base end side of the slit 30c—the base end of the aforementioned second high-frequency electrode manipulation member (not shown) is manipulated, and the second high-frequency electrode 32b is moved from the base end toward the distal end of the slit 30c, with the result that the second high-frequency electrode is held in the narrow part of the slit 30c where it presses against the outer circumferential face of the aforementioned portion of the desired tissue site of large diameter BV which is stopped at the mouth of the narrow part of the slit 30c. In this condition, while high-frequency current is flowing in the above-described manner to the first and second high-frequency electrodes 32a and 32b, if the cutter body 30 is pressed along with the second high-frequency electrode 32b toward the aforementioned portion of the desired tissue site of large diameter BV, the aforementioned portion of the desired tissue site of large diameter BV which has been pressed against the second high-frequency electrode 32b is severed by the high-frequency current which flows between the first high-frequency electrode 32a and second high-frequency electrode 32b, and the severed portion is clotted.

Next, a description of the configuration and operation of a sixth embodiment of the cutter 18 used in the body tissue harvesting instrument 10 illustrated in FIG. 1 is given, with reference to FIG. 8A and FIG. 8B. Most of the configuration of the sixth embodiment of the cutter 18 is identical to most of the configuration of the first embodiment of the cutter 18 which was described above with reference to FIG. 2A through FIG. 2C. Components of the sixth embodiment of the cutter 18 which are identical to the configuration of the first embodiment of the cutter 18 are given reference codes identical to the reference codes assigned to the corresponding components in the first embodiment of the cutter 18, and detailed description of these components is omitted.

The sixth embodiment of the cutter 18 differs from the first embodiment of the cutter 18 in that it is not provided with the feeding mechanism 34, instead of which the width of the distal end of the slit 30c of the cutter body 30 is set larger than the width of the base end of the slit 30c, and the second high-frequency electrode 32b in the slit 30c moves freely between the base end and a position near the distal end of the slit 30c. In further detail, in this embodiment, the slit 30c has a triangular shape where the base end constitutes one apex, or it forms a V-shape where the width widens as one moves from the base end toward the distal end. Furthermore, by means of a conventional energizing member 42 which is interposed between the cutter body 30 and the second high-frequency electrode 32b, the second high-frequency electrode 32b is impelled toward a position near the distal end of the slit 30c. The conventional energizing member 42 includes, for example, an elastic member typified by a spring or rubber.

In this sixth embodiment of the cutter 18, if there is a portion of a desired tissue site inside the body of an organism (e.g., a collateral venous branch of the aforementioned desired vein inside a leg) BV which is capable of being introduced into the distal end of the triangular or V-shaped slit 30c, it is possible to have the outer circumferential face of the aforementioned portion of the desired tissue site BV which has been introduced into the distal end of the triangular or V-shaped slit 30c exert pressure on the second high-frequency electrode 32b, and to press the second high-frequency electrode 32b against the outer circumferential face of the aforementioned portion of the desired tissue site BV by means of the energizing force of the conventional energizing member 42, which resists this pressure.

FIG. 8A shows a first condition where a portion of the aforementioned desired tissue site BV which has a diameter slightly larger than the width of the distal end of the slit 30c has been introduced into the triangular or V-shaped slit 30c, is held at the distal ends of the two side faces of the slit 30c, and is unable to move any further toward the base end of the slit 30c. Even in this first condition, as the outer circumferential face of the aforementioned portion of the desired tissue site of large diameter BV which is held at the distal ends of the two side faces of the slit 30c exerts pressure on the second high-frequency electrode 32b, the second high-frequency electrode 32b presses against the outer circumferential face of the aforementioned portion of the desired tissue site of large diameter BV by means of the energizing force of the conventional energizing member 42, which resists this pressure.

In this condition, while high-frequency current is flowing in the above-described manner to the first and second high-frequency electrodes 32a and 32b, if the cutter body 30 is pressed toward the aforementioned portion of the desired tissue site of large diameter BV, the aforementioned portion of the desired tissue site of large diameter BV which is pressed against the second high-frequency electrode 32b is severed by the high-frequency current which flows between the first high-frequency electrode 32a and second high-frequency electrode 32b, and the severed portion is clotted.

FIG. 8B shows a second condition where a portion of the aforementioned desired tissue site BV which has a diameter slightly larger than the width of the base end of the slit 30c has been introduced into the triangular or V-shaped slit 30c, and is held at a position near the base end of the two side faces of the slit 30c.

Even in this second condition, as the outer circumferential face of the aforementioned portion of the desired tissue site of small diameter BV which is held at a position near the base end of the two side faces of the slit 30c exerts pressure on the second high-frequency electrode 32b, the second high-frequency electrode 32b presses against the outer circumferential face of the aforementioned portion of the desired tissue site of small diameter BV by means of the energizing force of the conventional energizing member 42, which resists this pressure. In this condition, while high-frequency current is flowing in the above-described manner to the first and second high-frequency electrodes 32a and 32b, if the cutter body 30 is pressed toward the aforementioned portion of the desired tissue site of small diameter BV, the aforementioned portion of the desired tissue site of small diameter BV which is pressed against the second high-frequency electrode 32b is severed by the high-frequency current which flows between the first high-frequency electrode 32a and second high-frequency electrode 32b, and the severed portion is clotted.

The conventional energizing member 42 used in the sixth embodiment of the cutter 18 described above with reference to FIG. 8A and FIG. 8B would be able to function in a manner identical to the above-described case of the sixth embodiment of the cutter 18 were it to be interposed between the cutter body 30 and the second high-frequency electrode 32b in the fifth embodiment of the cutter 18 described above with reference to FIG. 7A and FIG. 7B.

Figure 9A:
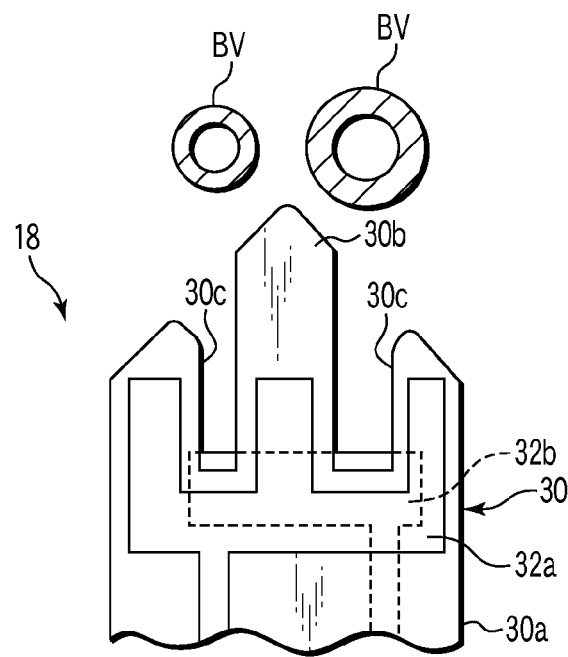
FIG. 9A and FIG. 9B are schematic plan views which sequentially show the procedure whereby a seventh embodiment of the cutter used in the body tissue harvesting instrument shown in FIG. 1 presses against in vivo body tissue (in this case, a vein in the leg of a human body), and severs the aforementioned body tissue.
Figure 9B:
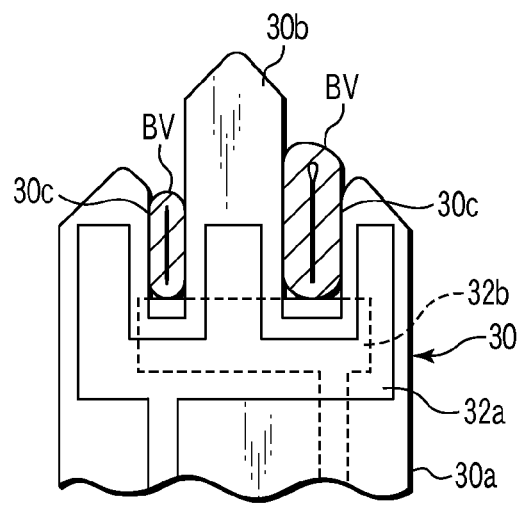

Next, a description of the configuration and operation of a seventh embodiment of the cutter 18 used in the body tissue harvesting instrument 10 illustrated in FIG. 1 is given, with reference to FIG. 9A and FIG. 9B. Most of the configuration of the seventh embodiment of the cutter 18 is identical to most of the configuration of the first embodiment of the cutter 18 which was described above with reference to FIG. 2A through FIG. 2C. Components of the seventh embodiment of the cutter 18 which are identical to the configuration of the first embodiment of the cutter 18 are given reference codes identical to the reference codes assigned to the corresponding components in the first embodiment of the cutter 18, and detailed description of these components is omitted.

The seventh embodiment of the cutter 18 differs from the first embodiment of the cutter 18 in that it is not provided with the feeding mechanism 34, instead of which multiple slits 30c whose respective widths differ are formed in the cutter body 30 so as to be mutually independent. The multiple slits 30c extend in a mutually parallel manner from the projecting end part 30b toward the base end part 30a of the cutter body 30. In this seventh embodiment of the cutter 18, illustrated in FIG. 9A and FIG. 9B, two slits 30c are formed in the cutter body 30, but the number of multiple slits 30c formed in the cutter body 30 may be more than two so long as the concept of this invention is followed.

In the seventh embodiment of the cutter 18 which is configured in the aforementioned manner, when a portion of a desired tissue site of large diameter inside the body of an organism BV which has a diameter slightly larger than the slit 30c of large width illustrated in FIG. 9A, and when a portion of a desired tissue site of small diameter inside the body of an organism BV which has a diameter slightly larger than the slit 30c of small width are respectively introduced into and flattened by the slit 30c of large width and the slit 30c of small width, they press against the second high-frequency electrode 32b at the base ends of the respective slits 30c as shown in FIG. 9B.

In this condition, while high-frequency current is flowing in the above-described manner to the first and second high-frequency electrodes 32a and 32b, if the cutter body 30 is pressed along with the second high-frequency electrode 32b toward the aforementioned portion of the desired tissue site of small diameter BV and toward the aforementioned portion of the desired tissue site of large diameter BV, the aforementioned portion of the desired tissue site of small diameter BV and the aforementioned portion of the desired tissue site of large diameter BV which have been pressed and flattened against the second high-frequency electrode 32b are severed by the high-frequency current which flows between the first high-frequency electrode 32a and second high-frequency electrode 32b, and the severed portion is clotted.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A body tissue harvesting instrument comprising:
an insertion member having a longitudinal axis and having a distal end and a proximal end wherein the distal end is inserted first into a body, and
a cutter which is provided at the distal end of the insertion member and which severs tissue inside the body,
wherein the cutter comprises:
a cutter body which includes a base end held at the distal end of the insertion member and a projection end which projects away from the distal end of the insertion member, wherein a slit is formed in the projection end extending toward the base end, and wherein the slit has two side edges extending from an opening at the projection end to a base edge,
a first high-frequency electrode disposed along the two side edges of the slit on the outer surface of the cutter body,
a second high-frequency electrode disposed at the base edge of the slit in the cutter body, and
a feeding mechanism arranged on the projection end of the cutter body with first and second rotating surfaces disposed along the two side edges respectively, which are rotated as a result of being pressed by the tissue, and which feed the tissue toward the base edge of the slit, wherein the first and second rotating surfaces are comprised of two rotary members disposed opposite each other along the two side edges of the slit, respectively, so that the first and second rotating surfaces move in a direction from the opening of the slit toward the base edge of the slit.

2. A body tissue harvesting instrument comprising:
an insertion member having a longitudinal axis and having a distal end and a proximal end wherein the distal end is inserted first into a body, and
a cutter which is provided at the distal end of the insertion member and which severs tissue inside the body,
wherein the cutter comprises:
a cutter body which includes a base end held at the distal end of the insertion member and a projection end which projects away from the distal end of the insertion member, wherein a slit is formed in the projection end extending toward the base end, and wherein the slit has two side edges extending from an opening at the projection end to a base edge,
a first high-frequency electrode disposed along the two side edges of the slit on the outer surface of the cutter body,
a second high-frequency electrode disposed at the base edge of the slit in the cutter body, and
a feeding mechanism arranged on the projection end of the cutter body with first and second rotating surfaces disposed along the two side edges respectively, which are rotated as a result of being pressed by the tissue, and which feed the tissue toward the base edge of the slit, wherein the first and second rotating surfaces are comprised of two rotary members disposed opposite each other along the two side edges of the slit, respectively, so that the first and second rotating surfaces move in a direction from the opening of the slit toward the base edge of the slit;
wherein the feeding mechanism of the cutter further comprises two subsidiary rotary members disposed opposite each other along the two side edges of the slit, respectively, and having third and fourth rotating surfaces configured to move in the direction from the opening of the slit toward the base edge of the slit, and two belt members which engage between each of the two rotary members and a respective one of the two subsidiary rotary members so that the belt members each has a respective surface disposed along a respective one of the two side edges of the slit that moves in the direction from the opening of the slit toward the base edge of the slit to feed the tissue toward the base edge of the slit.

* * * * *

UNITED STATES PATENT AND TRADEMARK OFFICE
CERTIFICATE OF CORRECTION

PATENT NO. : 8,298,229 B2  
APPLICATION NO. : 12/136388  
DATED : October 30, 2012  
INVENTOR(S) : Akihito Kano et al.

Page 1 of 1

It is certified that error appears in the above-identified patent and that said Letters Patent is hereby corrected as shown below:

On the title page, under (75) Inventors, change "Randal J. Kadyowski" to --Randal J. Kadykowski--.

Signed and Sealed this  
Twenty-sixth Day of February, 2013

Teresa Stanek Rea  
*Acting Director of the United States Patent and Trademark Office*